United States Patent
Weber-Unger et al.

[11] Patent Number: 5,603,791
[45] Date of Patent: Feb. 18, 1997

[54] METHOD OF MAKING BREAST PROSTHESIS

[75] Inventors: Georg Weber-Unger, Kufstein, Austria; Stephan Volk, Miesbach, Germany

[73] Assignee: Dr. Helbig GmbH & Co. Orthopädische Produkte, Brannenburg, Germany

[21] Appl. No.: 442,357

[22] Filed: May 16, 1995

Related U.S. Application Data

[62] Division of Ser. No. 299,755, Sep. 1, 1994, abandoned.

[30] Foreign Application Priority Data

Jun. 20, 1994 [DE] Germany ................ 44 21 516.9

[51] Int. Cl.$^6$ ................ A61F 2/52; B32B 31/04; B32B 31/06; B32B 31/26
[52] U.S. Cl. ................ 156/145; 156/245; 156/267; 156/290; 623/7
[58] Field of Search ................ 623/7, 8; 450/32, 450/38, 53–57; 2/267; 156/145, 245, 267, 290, 307.1, 308.4

[56] References Cited

U.S. PATENT DOCUMENTS

| | | | |
|---|---|---|---|
| 2,636,182 | 4/1953 | Freedman | 623/7 |
| 3,845,507 | 11/1974 | Kirby et al. | 623/7 |
| 4,185,332 | 1/1980 | Jahnig | 623/7 |
| 4,247,351 | 1/1981 | Rechenberg | 156/245 X |
| 4,249,975 | 2/1981 | Rechenberg | 156/245 |
| 4,380,569 | 4/1983 | Shaw | 623/7 X |
| 5,071,433 | 12/1991 | Naestoft et al. | 623/7 |
| 5,092,881 | 3/1992 | Weber-Unger et al. | 623/8 |
| 5,347,656 | 9/1994 | Fabritz et al. | 450/38 X |

FOREIGN PATENT DOCUMENTS

| | | | |
|---|---|---|---|
| 2094826 | 2/1972 | France | 623/7 |
| 2457041 | 6/1976 | Germany | 623/7 |
| 2827077 | 1/1980 | Germany | 623/7 |

Primary Examiner—Adrienne C. Johnstone
Attorney, Agent, or Firm—Henry M. Feiereisen

[57] ABSTRACT

A breast prosthesis to be worn on the body of a person who has had a mastectomy includes a soft-elastic prosthetic body made of two plastic sheets which are connected to each other along a common edge, with a plastic mass being contained hollow-free between the plastic sheets. The prosthetic body has a front side resembling in its form the natural breast and a rear side which faces the wearer's body. A fabric member covers the rear side and is attached solely to the peripheral edge of the plastic sheets of the prosthetic body to thereby increase the comfort of wearing the breast prosthesis. The fabric member is suitably made of thermoplastic material, with the welding of the plastic sheets and the welding of the fabric member with the plastic sheets being carried out in a single working step.

2 Claims, 1 Drawing Sheet

METHOD OF MAKING BREAST PROSTHESIS

This is a division of application Ser. No. 08/299,755, filed Sep. 1, 1994 now abandonded.

BACKGROUND OF THE INVENTION

The present invention refers to a breast prosthesis to be worn on the body of a person who has had a mastectomy, and in particular to a breast prosthesis of a type having a soft elastic prosthetic body comprised of two plastic sheets connected to each other along a common edge and a plastic mass enclosed hollow-free between the plastic sheets, with the prosthetic body having a front side resembling in its form the natural breast and a rear side which faces a wearer's body, and a fabric member which spans the rear side and is attached to the prosthetic body. The present invention further relates to a method for making a breast prosthesis.

German publication DE-OS 28 27 077 discloses a breast prosthesis of this type, with the plastic sheet that is arranged on the rear side of the prosthetic body being coated with a fabric member in form of a textile, knitted fabric or web. The fabric member is made of cotton material which is sweat-absorbing, with the fabric member and the plastic sheet being joined together coextensively over their entire area. Thus, no hollow is formed between the plastic sheet and the fabric member through which moisture absorbed by the fabric member could exit. At prolonged sweat absorption, the fabric member becomes increasingly moist so that the prosthesis will stick or cling to the wearer's skin and will cause uncomfort for the wearer of the prosthesis because of evaporative cooling which leaves an unpleasant cold feeling on the wearer's skin.

These drawbacks which result from coating the one plastic sheet arranged on the rear side of the prosthetic body with a fabric member are not encountered when loosely disposing the prosthesis within a completely surrounding fabric pocket, as known for example from U.S. Pat. No. 4,795,464. This prosthesis has a rear side which forms a depression, and a cushion body which follows the contour of the rear side of the prosthetic body and is detachably held in the depression by the fabric pocket which surrounds the prosthetic body on the front side. The fabric pocket is made of elastic cotton material, with the section of the fabric pocket forming the rear side thereof bearing on the wearer's skin to enable absorbed sweat to be carried off into the depression and to eliminate the formation of a moisture accumulation in this fabric section. The transport of moisture from the fabric section is further enhanced by the pump effect created through the relative movement between the prosthetic body and the fabric section. Still, the provision of a fabric pocket of this type has drawbacks because the costs for manufacturing such a fabric pocket are comparably high and the prosthesis shifts and becomes displaced relative to the fabric pocket during wearing.

SUMMARY OF THE INVENTION

It is an object of the present invention to provide an improved breast prosthesis obviating the aforestated drawbacks.

In particular, it is an object of the present invention to provide an improved breast prosthesis by which perspiration on the skin is rapidly carried off, without requiring the use of a fabric pocket.

It is a further object of the present invention to provide an improved method for making a breast prosthesis.

These objects, and others which will become apparent hereinafter are attained in accordance with the present invention by providing the prosthesis with a fabric member which is securely attached to the plastic sheets only along the peripheral edge.

By connecting the fabric member only along the periphery of the plastic sheets, the breast prosthesis is provided inside the peripheral area of the prosthesis with a zone in which the fabric member is not fixedly secured to the adjacent plastic sheet that is located on the rear side of the prosthetic body. Skin perspiration absorbed by the fabric member can thus be carried off to the area between the fabric member and the rear side of the prosthetic body. Thus, moisture is prevented from accumulating in the fabric member, thereby diminishing the tendency to stick to the wearer's skin so that the fabric member feels comfortable when worn on the skin.

The area between the fabric member and the rear side of the prosthetic body may be formed by a single hollow when the rear side of the prosthetic body is provided with a depression as provided in conventional shell-type prostheses. By reinforcing the depression in a conventional manner, several compartments are formed between the fabric member and the rear side of the prosthetic body. However, when the rear side of the prosthetic body is flat as known in so-called full prostheses, the fabric member bears loosely on the rear side of the prosthetic body when the prosthetic body and the fabric member are not deformed. Since a movement of the wearer results in an elastic deformation of the prosthesis, the fabric member will not permanently lie against the rear side of the prosthetic body but will be lifted off more or less from the rear side in accordance with the elastic deformation of the prosthesis so that a space or spaces of varying sizes are obtained in the area between the fabric member and the rear side of the prosthetic body.

Moisture is continuously carried off from the fabric member into the area between the fabric member and the rear side of the prosthetic body regardless whether the fabric member bears loosely on the rear side of the prosthetic body, or one or several hollow spaces are formed between the fabric member and the rear side. Hollow spaces between the fabric member and the rear side of the prosthetic body enhance the absorption of moisture in the area therebetween and promote an air circulation in this region so that condensation of contained moisture is created even more rapidly.

The breast prosthesis according to the present invention can be made in a more cost-efficient manner than conventional prostheses because the provision of a fabric pocket is not required which otherwise complicates the manufacture and results in an increased demand of material compared to the fabric member of the prosthesis according to the invention.

The breast prosthesis according to the present invention combines the advantages of a prosthesis with fabric pocket and a prosthesis having a rear side coated with a textile material, without encountering the drawbacks associated with these conventional prostheses. Thus, the prosthesis according to the invention is highly comfortable to wear and prevents irritation to the wearer's body.

The fabric member can be made of a thermoplastic material and is suitably welded to the perimeter of the plastic sheets. In this manner, the fabric member is securely and permanently joined with the prosthetic body. The welded connection is especially advantageous when both plastic sheets are also joined together through welding because the joining of the plastic sheets and the connection of the fabric member to the prosthetic body can be carried out by a same process. It will be understood that a welding of the fabric member with the plastic sheets does not necessarily mean that the fabric member is completely fused together along the weld with the plastic sheets. The term "welding" should also mean to refer to an attachment in which the fabric member is fused with the plastic sheets only on its surface.

Instead of being welded to the prosthetic body, the fabric member may also be glued to the peripheral edge of the plastic sheets. A gluing will also result in a secure, and permanent connection between the fabric member and the prosthetic body and is especially suitable when using materials for the fabric member which are less appropriate for welding, e.g. when making the fabric member wholly or partly of natural fibers such as cotton.

The fixed connection between the fabric member and the prosthetic body enables a flush alignment of the edge of the fabric member with the edge of the plastIC sheets. In contrast thereto, conventional fabric pockets always projects beyond the prosthesis rim because a border forms along the rim of the prosthesis for joining together the forward part and the rear part of the fabric pocket. A protruding border is however undesired because it may peek out of the garment in which the prosthesis is worn.

The fixed connection between the fabric member and the prosthetic body enables also a securement of the prosthesis to the garment via the fabric member Thus, in accordance with another feature of the present invention, the fabric member provided with a rim area which at least in sections projects beyond the perimeter of the plastic sheets and is secured via a suitable fastener to a bra or a top part of a bathing suit in which the prosthesis is worn. For example, the fastener may include one or several Velcro fasteners, with the counterpiece being secured to the garment.

The fabric member can be made of various materials. Criteria for selection of a suitable material for the fabric member include easy attachment to the prosthetic body, a good stretching ability, a high resistance to tearing, a good moisture absorption and moisture discharge capability, a pleasant softness and easy cleaning. For welding purposes, it is advantageous to make the fabric member of polyamide fibers or polyester fibers. Other materials for the fabric member may also include cotton or a mixture of polyamide fibers and/or polyester fibers and cotton. These materials are known to have skin friendly properties. When being made completely of cotton, the fabric member is preferably glued to the prosthetic body. When demanding a high stretching ability of the fabric member, e.g. in cases after partial mastectomies when the fabric member should closely bear upon the remaining breast tissue without exerting any pressure to the surgical scar, it is advantageous to make the fabric member with a fiber content of polyester fibers and/or polyamide fibers and a fiber content of elastofibers. If it is desired to provide the fabric member with a particular capability to carry off moisture from the skin surface, it is advantageous to make the fabric member from a web of microfibers by which moisture in form of vapor can be transported off. In particular suitable are superfine fibrilated microfibers which are made of polyester or polyamide. Such microfiber webs are conventionally known as "Klimastoffe" (climatic materials) because of their ability to allow vaporized body sweat to condense through the fabric.

A method of making a breast prosthesis to be worn on the body of a person who has had a mastectomy includes preparing a bag with an inlet opening by welding two adjacent and coextensive polyurethane sheets along a common line which later forms the prosthesis rim, introducing a non-vulcanized silicone rubber through the inlet opening of the bag while the filled bag is arranged in a mold preferably a single-split mold, with a cavity conforming to the front side of the prosthesis which resembles the natural breast and attaching a fabric member to the rear side of the prosthesis, with the fabric member being made of a thermoplastic material, and with the fabric member and the polyurethane sheets being welded together during welding of both sheets in such a manner that the fabric member is secured only about the later peripheral edge of the prosthesis.

The method according to the invention has the advantage that the attachment of fabric member to the polyurethane sheets can be carried out simultaneously with the welding of the polyurethane sheets. Thus, only a single welding process is required during which the polyurethane sheets and the fabric member are welded together about the periphery of the prosthesis. The bag made in this manner is then placed in a single-split mold with the fabric member facing upwards and filled with the non-vulcanized silicone rubber. Then, the single-split mold is closed and the bag is heated, preferably by placing the mold in a heating cabinet, to cross-link the silicone rubber through application of heat. After cross-linking of the silicone rubber, the single-split mold is removed from the heating cabinet and opened. The molded article comprised of bag, cross-linked silicone rubber and welded-on fabric member corresponds essentially to the configuration of the later prosthesis and is ejected from the single-split mold for final processing which includes separating the still projecting border area of the polyurethane sheets and of the fabric member up to the weld which then forms the perimeter of the finished prosthesis.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
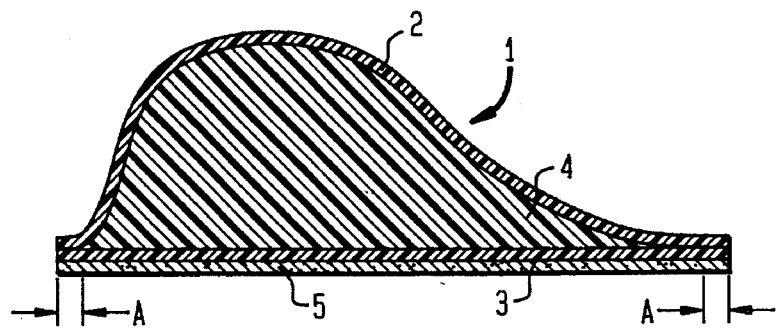
FIG. 1 is a cross sectional view of one embodiment of a breast prosthesis according to the present invention, designed as a full prosthesis.

Throughout all the Figures, the same or corresponding elements are always indicated by the same reference numerals.

Turning now to the drawing, and in particular to FIG. 1, there is shown a cross sectional view of one embodiment of a breast prosthesis according to the present invention, including a prosthetic body 1 of soft elastic plastic material. The prosthesis body 1 is comprised of two polyurethane sheets 2, 3 which are welded together along their common periphery in an area designated A, with an additive cross-linked two-component silicone rubber 4 being snugly fitted hollow-free between the polyurethane sheets 2, 3. The polyurethane sheet 2 represents the front side of the prosthetic body 1 and resembles the configuration of the natural breast. The polyurethane sheet 3 represents the rear side of the prosthetic body 1 and faces the wearer's body.

Covering the rear side of the prosthetic body 1 is a fabric member 5 which is welded in the area A in which the polyurethane sheets 2, 3 are welded together to the polyurethane sheets 2, 3 for attachment to the prosthetic body 1. The fabric member 5 is thus securely attached only about the peripheral edge of the polyurethane sheet 2, 3, while being detached or loose in the area inside the region A.

In the breast prosthesis as illustrated in FIG. 1, the rear side of the prosthetic body 1 is of flat configuration so that this type of breast prosthesis is called a "full prosthesis". The fabric member 5 loosely bears inside the area A upon the polyurethane sheet 3.

When the breast prosthesis is elastically deformed e.g. through movement, chambers can form between the fabric member 5 and the polyurethane sheet 3 of a size which depends on the extent of deformation of the prosthesis. These chambers absorb and release air through the fabric member 5 so that the body area which is covered by the prosthesis is comfortably ventilated. The ventilation also counteracts a perspiration in this chamber area. In case sweat is encountered despite ventilation, this sweat is absorbed by the fabric member 5 and carried off into the area between the polyurethane sheet 3 and the fabric member 5. Therefore, no unpleasant cooling sweat remains upon the skin.

Figure 2:
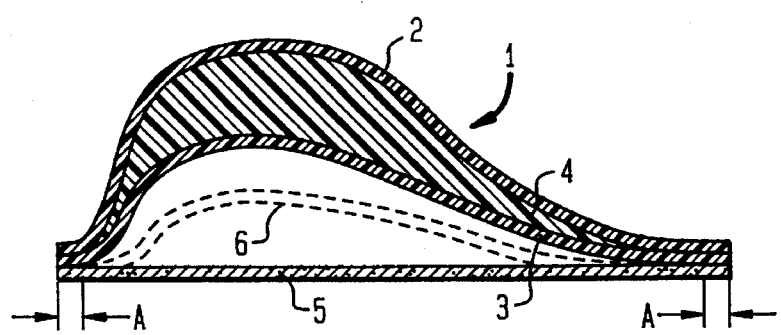
FIG. 2 is a cross sectional view of a second embodiment of a breast prosthesis according to the present invention, having a prosthetic body with a rear side forming a depression.

Turning now to FIG. 2, there is shown a second embodiment of a breast prosthesis 1 according to the present invention which differs from the breast prosthesis of FIG. 1 by the provision of a depression 6 on the rear side of the prosthetic body 1. The polyurethane sheet 3 located on the rear side of the prosthetic body 1 follows the contour of the depression 6. Such a breast prosthesis is commonly known as a "shell-type prosthesis". The polyurethane sheets 2, 3 are welded together in the area A and with the fabric member 5. In contrast to the breast prosthesis illustrated in FIG. 1, the fabric member 5 does not loosely bear inside the area A upon the polyurethane sheet 3 but spans the depression 6. The fabric member 5 is soft and elastic and thus can easily adapt to the configuration of the breast tissue which remains after a partial mastectomy and project into the depression 6 as indicated by the broken double line in FIG. 2. Also in a deformed position of the fabric member 5, a space is created in the area between the fabric member 5 and the polyurethane sheet 3 for air to enter and to exit and thereby to effect a ventilation of the body area covered by the prosthesis. This space is in most cases significantly greater than the space formed between the fabric member 5 and the polyurethane sheet 3 in the embodiment of the breast prosthesis of FIG. 1 so that the air exchange is improved compared to the prosthesis illustrated in FIG. 1. The improved air exchange results in a more rapid condensation of moisture transported into the space between the fabric member 5 and the polyurethane sheet 3 so that the moisture absorption and moisture discharge of the fabric ember 5 of the breast prosthesis of FIG. 2 is even more enhanced compared to the prosthesis illustrated in FIG. 1.

Figure 3:
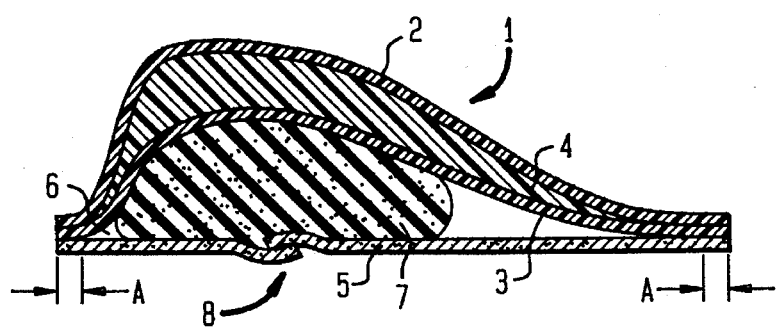
FIG. 3 is a cross sectional view of a third embodiment of a breast prosthesis according to the present invention, with a cushion body being disposed in the depression of the rear side.

FIG. 3 illustrates a third embodiment of a breast prosthesis 1 according to the present invention which is provided with a depression 6 similar to the breast prosthesis illustrated in FIG. 2. In order to prevent a collapse of such a prosthesis through its own weight in particular when the prosthesis is of great dimension, a cushion body 7 is disposed within the depression 6 between the fabric member 5 and the polyurethane sheet 3. The cushion body 7 may be made for example of plastic foam or may be a tangle of fiber which is surrounded by a not shown bag.

Also in the breast prosthesis 1 of FIG. 3, the fabric member 5 is welded only in the peripheral area A with the polyurethane sheet 2, 3, while in the zone inside the peripheral area A, the fabric member 5 is not securely fixed to the prosthetic body 1. The fabric member 5 extends loosely on the cushion body 7 and includes a slit-like opening 8 which is closable by two overlapping ends of the rear side of the fabric member 5. The cushion body 7 can be introduced into and removed from the depression 6 through this opening 8.

Like in the breast prosthesis 1 of in FIG. 2, the fabric member 5 effects a good ventilation and sweat discharge in the body area which is covered by the prosthesis.

Figure 4:
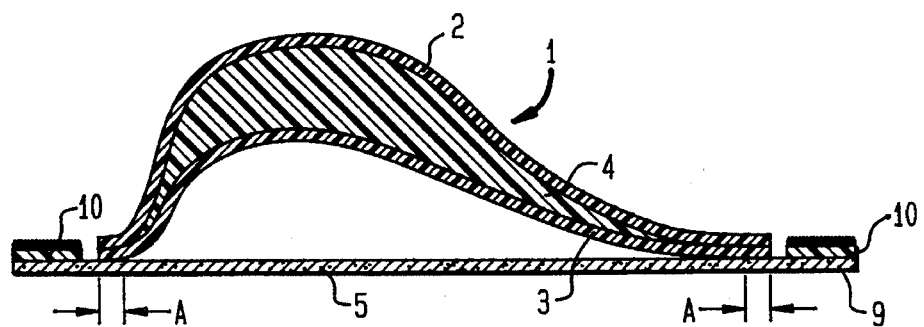
FIG. 4 is a cross sectional view of a fourth embodiment of a breast prosthesis according of the present invention, with the fabric member having a border zone projecting beyond the perimeter of the prosthetic body for attachment of a garment.

FIG. 4 shows a fourth embodiment of a breast prosthesis 1 similar to the prosthesis of FIG. 2, with the difference residing in the provision of the fabric member 5 with a border section 9 which projects beyond the perimeter of the prosthesis formed by the polyurethane sheets 2, 3. The border section 9 is provided with a Velcro® fastener 10 which has a counterpiece (not shown) attached to the bra or top part of a bathing suit in which a prosthesis is worn. Through attachment via the Velcro® fastener 10, the prosthesis can be secured upon the garment against undesired slipping or turning. The fabric member 5 is also only welded about the peripheral area A to the polyurethane sheets 2, 3 and thus secured to the prosthetic body 1.

Like the breast prosthesis 1 of FIG. 2, the breast prosthesis 1 of FIG. 4 is characterized by superior ventilation and transport of moisture.

A suitable material for the fabric member 5 includes microfibers, available under the designation "Ninfea" sold by the company Jersey Lomellina SPA, Italy, which includes 75% Nylon® and 25% Elastan®.

In accordance with a method for making a breast prosthesis according to the present invention, both polyurethane sheets 2, 3 and the fabric member 4 are placed adjacent to and coextensive with each other and welded together, except for an inlet opening which is later to be closed, about a line which later forms the perimeter of the prosthesis, to thereby provide a bag. The bag is then placed in a single-split mold with the fabric member 5 facing upwardly and filled with non-vulcanized silicone rubber. The single-split mold is then closed and placed in a heating cabinet for cross-linking the silicone rubber. After cross-linking the silicon rubber, the single-split mold is removed from the heating cabinet and opened. The molded article comprised of bag, cross-linked silicone rubber and welded-on fabric member has already a shape which essentially resembles the final prosthesis and is removed from the single-split mold for final processing.

During final processing, the border section of the fabric member 5 and the border section of the polyurethane sheets 2, 3 project beyond the perimeter of the final prosthesis and are thus separated. Thus, the attachment of the fabric member 5 to the polyurethane sheets 2, 3 and the final processing of the prosthesis does not require an additional working step compared to conventional methods (as far as the method is concerned for making prosthesis according to FIGS. 1–3).

In the breast prosthesis according to FIG. 4 the welding is effected in a same manner as described in reference to the breast prostheses of FIGS. 1–3, while the final processing of the prosthesis shown in FIG. 4 differs in such a manner that the border section 9 of the fabric member 5 which projects beyond the perimeter of the final prosthesis is retained at least along segments for allowing attachment of the Velcro® fastener 10.

While the invention has been illustrated and described as embodied in a breast prosthesis, it is not intended to be limited to the details shown since various modifications and structural changes may be made without departing in any way from the spirit of the present invention.

What is claimed as new and desired to be protected by Letters Patent is set forth in the appended claims:

1. A method of making a breast prosthesis to be worn on the body of a person who has had a mastectomy, comprising the steps of:

forming a bag with an inlet opening by suitably welding two plastic sheets to each other along a common weld which later defines the perimeter of the prosthesis and welding a fabric member of thermoplastic material to one side of the bag only along the common weld, which fabric member later defines the rear side of the prosthesis;

placing the bag in a mold having a cavity of a configuration corresponding to the front side of the prosthesis resembling the person's natural breast;

introducing a non-vulcanized silicone rubber through the inlet opening of the bag; and applying heat to the bag to cross-link the silicone rubber.

2. The method of claim 1 wherein the plastic sheets and the fabric member have a border section which projects beyond the perimeter and is separated up to the weld after said heat applying step in a final processing step.

* * * * *